(12) United States Patent
Lauren et al.

(10) Patent No.: US 6,786,718 B2
(45) Date of Patent: Sep. 7, 2004

(54) TOOL AND METHOD FOR ADJUSTING ORTHODONTIC EXPANSION SCREWS

(75) Inventors: Mark D. Lauren, Amherst, NY (US); Stephen P. Warunek, Lancaster, NY (US)

(73) Assignee: Great Lakes Orthodontics, Ltd., Tonawanda, NY (US)

( * ) Notice: Subject to any disclaimer, the term of this patent is extended or adjusted under 35 U.S.C. 154(b) by 0 days.

(21) Appl. No.: 10/165,011

(22) Filed: Jun. 6, 2002

(65) Prior Publication Data

US 2003/0013061 A1 Jan. 16, 2003

Related U.S. Application Data

(60) Provisional application No. 60/296,255, filed on Jun. 6, 2001.

(51) Int. Cl.[7] .................................................. A61C 3/00
(52) U.S. Cl. .......................................... 433/3; 433/141
(58) Field of Search ............................... 433/3, 4, 141; 81/450

(56) References Cited

U.S. PATENT DOCUMENTS

| | | | |
|---|---|---|---|
| 4,028,968 A | * 6/1977 | DeAmicis | 81/450 |
| 4,996,896 A | * 3/1991 | Bachand | 81/450 |
| 5,040,975 A | * 8/1991 | Ettwein et al. | 433/3 |
| 5,133,659 A | * 7/1992 | Shilliday | 433/3 |
| 5,423,677 A | * 6/1995 | Brattesani | 433/72 |

* cited by examiner

Primary Examiner—John J. Wilson
(74) Attorney, Agent, or Firm—Hodgson Russ LLP

(57) ABSTRACT

An adjusting tool and associated method of use for turning orthodontic expansion screws are described. The tool or device consists of a contra-angled molded plastic handle or housing with a rotatable pin at the distal end for inserting into an expansion screw located in a patient's mouth. The tool housing is designed to limit the angular rotation of the pin to the arc required for insertion and subsequent activation of the orthodontic screw. When rotated to the position associated with screw activation, the pin is captured and held in place by a locking mechanism which then requires the tool to be disengaged from the screw prior to its removal from the patient's mouth. This feature eliminates the possibility of reversing and deactivating the expansion screw by pulling the expansion key straight out of the mouth. A manual release mechanism on the tool frees the pin to allow the pin to be rotated back to the insertion position. A built-in light assists with sighting the end of the wire and the insertion holes in the expansion screw.

21 Claims, 5 Drawing Sheets

TOOL AND METHOD FOR ADJUSTING ORTHODONTIC EXPANSION SCREWS

CROSS REFERENCE TO A RELATED APPLICATION

Applicants hereby claim priority based on U.S Provisional Patent Application No. 60/296,255 filed Jun. 6, 2001 and entitled "Tool And Method For Adjusting Orthodontic Expansion Screws" which is incorporated herein by reference.

BACKGROUND OF THE INVENTION

Expansion screws that utilize an opposing thread design have been used in orthodontic appliances for about 100 years. Typically, a central hub in the screw contains two through-holes 90° apart. The holes allow a pin such as that designated 10 in FIG. 1 to be inserted to rotate the screw and expand two movable bodies that run on the screw threads. The spreading apart of the screw bodies effects a uniaxial extension which is incorporated into orthodontic appliances to effect a variety of treatments.

The screw is captured by a stationary component which can be a housing or simply a parallel shaft which is typically designed to allow only a ¼ turn of the screw each time the 'activating' pin is inserted into the central hub. To advance the screw another ¼ turn, a single 'activation', the pin must be disengaged from the screw and reinserted. The tools or keys currently used to activate or turn such screws are very simple in design. Low cost significantly dictates the design of many high-volume orthodontic products. A straight length of wire, typically 0.040 inch in diameter, with a small loop for pinching between the fingers has been used for many years. Special plastic safety attachments are also known for preventing such keys from being swallowed.

In 1966, Soloveichik (USSR Patent No. #189,125) described a key device for turning orthodontic expansion screws consisting of a rotatable pin fitted to the end of a handle. Use of the device was also described as consisting of: 1) inserting the pin into the openings in an expansion screw, and 2) moving the handle along its long axis to rotate the pin on its axis while effecting rotation the expansion screw. Rotation of the screw is described as being related to the hinged union between the pin and the handle. Soloveichik describes the hinges as being threaded to the handle to facilitate replacement of the pin.

Schilliday (U.S. Pat. No. #5,133,659 1992) describes a similar-purposed orthodontic key consisting of a plastic handle designated 16 in FIG. 2 and freely rotating pin 18 at one end. Schilliday describes a plastic rivet for attaching the pin to the handle instead of a screw as described by Soloveichik. Both the Soloveichik and Schilliday designs have freely rotating pins (through 360°) at the end of a handle.

While such tools are simple and inexpensive to produce, it is known that the free and reversible rotation of the pin can lead to a failed activation the orthodontic screw. If the pin is not disengaged from the screw after turning the screw ¼ turn, back-rotation of the screw can take place when removing the tool from the mouth. This reversing action negates the positive screw activation just performed.

The turning of orthodontic screws is performed at home by the patient, or the patient's parent. Typically, the screw is turned ¼ revolution (one activation) once or twice daily. The tool provided by the orthodontist must be simple to use and reliable to assist patient compliance and ensure that the doctor's schedule for activation is followed. Failure to activate orthodontic screws leads to delayed treatment times and increased office visits. The steady expansion desired for this type of treatment is also affected.

SUMMARY OF THE INVENTION

The orthodontic tool of this invention functions to restrict rotation of the pin and to capture the pin at a specific angle. The tool also provides for releasing the captured pin. Capture of the pin by the tool following screw activation requires the disengagement of the pin from the screw prior to removing the tool from the mouth. This overcomes the possibility of back-driving the screw and negating the activation.

In particular, an adjusting tool and associated method of use for turning orthodontic expansion screws are described. The tool or device can comprise a contra-angled molded plastic handle or housing with a rotatable pin at the distal end for inserting into an expansion screw located in a patient's mouth. The tool housing is designed to limit the angular rotation of the pin to the arc required for insertion and subsequent activation of the orthodontic screw. When rotated to the position associated with screw activation, the pin is captured and held in place by a locking mechanism which then requires the tool to be disengaged from the screw prior to its removal from the patient's mouth. This feature eliminates the possibility of reversing and deactivating the expansion screw by pulling the expansion key straight out of the mouth. A manual release capability of the tool frees the pin to allow the pin to be rotated back to the insertion position after it has been removed from the mouth. A built-in light assists with sighting the end of the wire and the insertion holes in the expansion screw.

The foregoing and additional advantages and characterizing features of the present invention will become clearly apparent upon a reading of the ensuing detailed description together with the included drawing. The following detailed description of the invention, when read in conjunction with the accompanying drawings, is in such full, clear, concise and exact terms as to enable any person skilled in the art to which it pertains, or with which it is most nearly connected, to make and use the invention.

DESCRIPTION OF THE INVENTION

Figure 1:
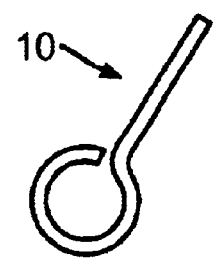
FIG. 1 is a side elevational view of a prior art pin for adjusting orthodontic expansion screws.
Figure 2:
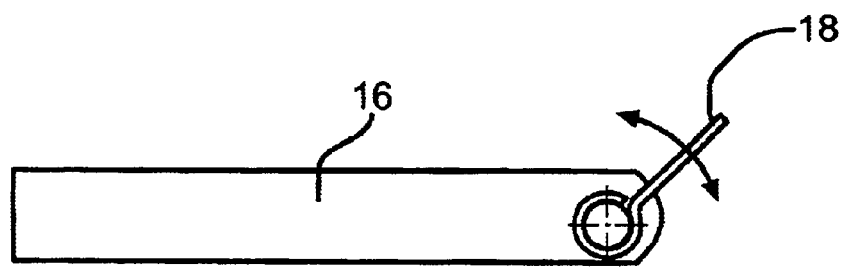
FIG. 2 is a side elevational view of another prior art device for adjusting orthodontic expansion screws.
Figure 3:
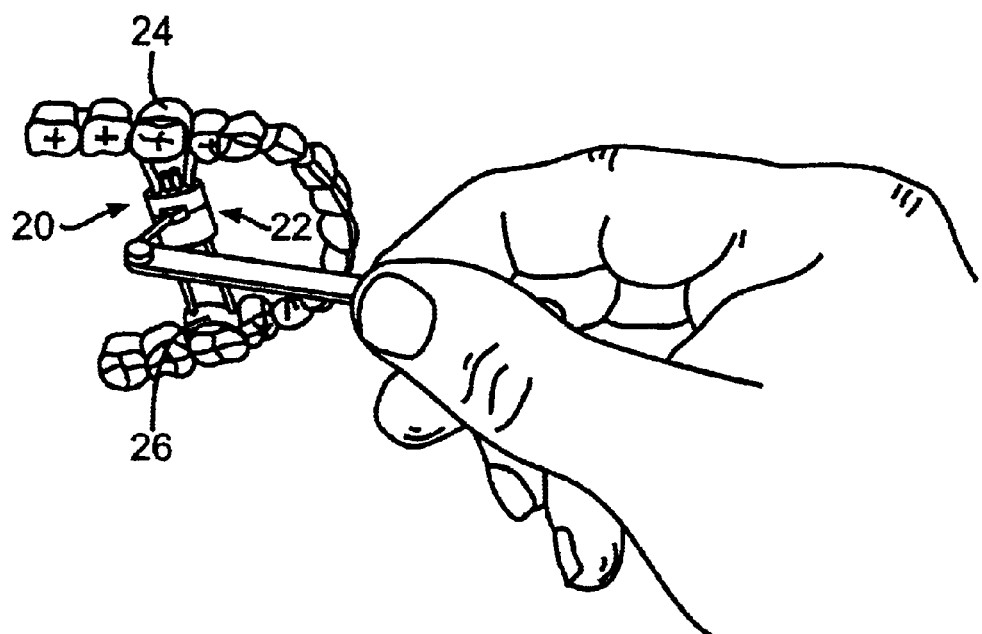
FIG. 3 is a perspective view illustrating one form of orthodontic expansion screw which can be adjusted by the tool according to the present invention.

This invention is a tool and method for turning orthodontic expansion screws. An example of such an expansion screw is shown in U.S. Pat. No. 5,133,659 issued Jul. 28, 1992 the disclosure of which is hereby incorporated by reference. By way of illustration, FIG. 1 of that patent is partially reproduced in FIG. 3 herein to show a palatal expander appliance 20 installed in a patient's mouth. The appliance includes the expansion screw 22 which is attached at opposite ends to the patient's teeth by means of bands 24, 26. Also shown is the prior art tool of FIG. 2 being used to turn the expansion screw for making an adjustment.

Figure 4:
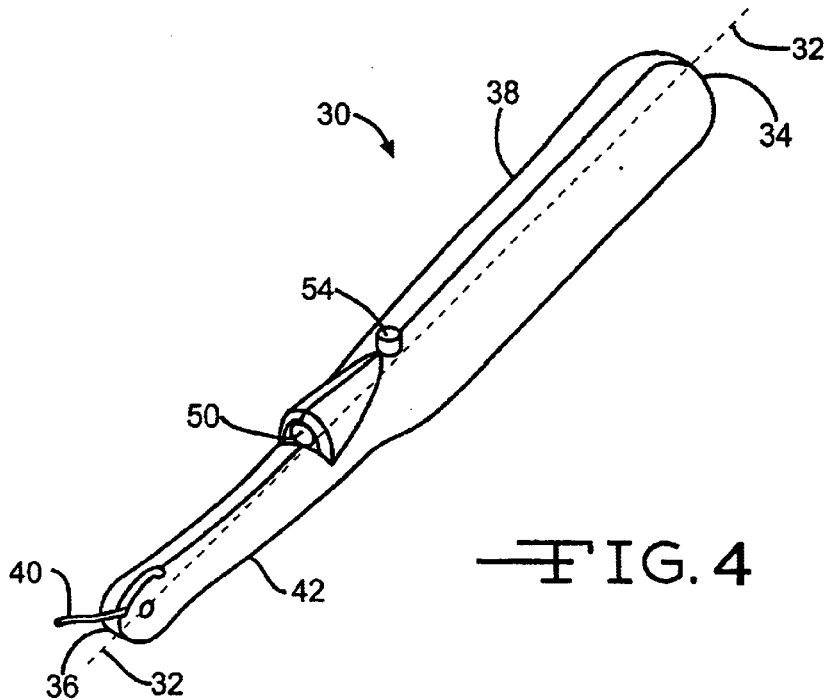
FIG. 4 is a perspective view of the tool of the present invention.

One form of the tool or device of the present invention comprises a hand-held instrument designated 30 in FIG. 4 having a body preferably made of two injection molded plastic halves. The instrument body has a longitudinal axis 32 and substantially opposite ends 34 and 36. A handle portion 38 extends longitudinally inwardly from end 34 for grasping by the hand of a user. A pivotal rotatable key in the form of a pin 40, typically 0.040 inch in diameter, is located at the distal end 36 of the device. A front portion 42 of the device extends between the distal end 36 and the handle portion 38. The pin 40 is designed to engage an orthodontic expansion screw of the type shown in FIG. 3 inside a patient's mouth. Pivotal or rotation movement of the pin 40 is restricted to an arc ranging from pin insertion to full activation of the orthodontic screw. In particular, the key or pin 40 is movably carried by the tool body 30 near the distal end 36 for movement along an angular path in a plane substantially parallel to the longitudinal axis 32 of body 30 so that upon engagement between key 40 and the orthodontic expansion screw the screw is rotated in response to movement of tool body 30 manually by the user in a direction generally parallel to longitudinal axis 32 causing key 40 to move along the angular path from the beginning of the path to the end of the path.

There is also provided a holding means which will be described in detail presently which releasably captures the pin 40 when it rotates or pivots into position following activation of the screw. This prevents back-rotation of the screw. The tool also provides for manual release to free the captured pin and allow repeated rotation as will be described in detail presently. The tool is designed with a contra-angle to provide a more convenient insertion angle and field of view into the mouth.

Figure 5:
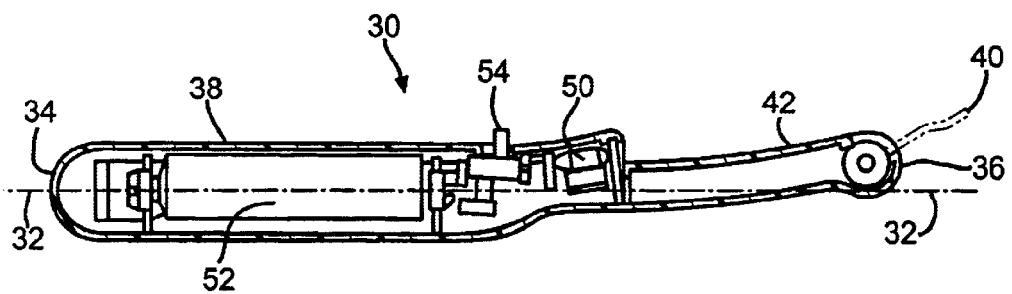
FIG. 5 is a longitudinal sectional view of the tool of FIG. 4.

A light source 50 is also incorporated in the tool to assist with sighting the hole in the expansion screw as well as the end of pin 40. As shown in FIG. 5, light source 50 is a lamp powered by a battery 52 mounted within the body of tool 30 and controlled by a switch 54 in a known manner. The pin may also be coated with a reflecting material or paint to assist visualizing the wire. The casing or body of tool 30 may be designed to hermetically seal the battery compartment for safety.

Figure 6:
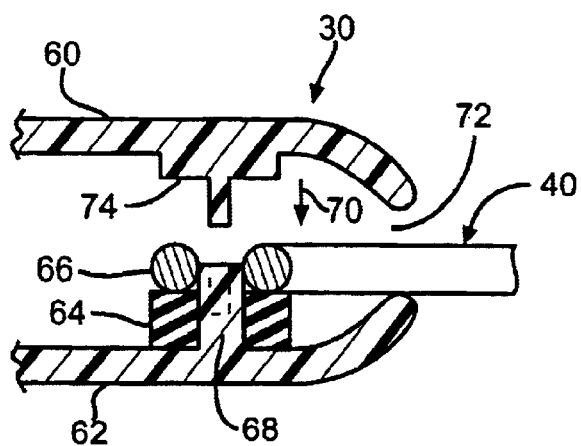
FIG. 6 is an enlarged fragmentary developed view showing the pivotal connection of the key in the housing of the tool of the present invention.

FIG. 6 is an enlarged, fragmentary developed view showing the pivotal or rotatable connection of the key or pin 40 in the body of tool 30. The housing of tool 30 preferably comprises two half shells, portions of which are designated 60 and 62 in FIG. 6, typically of plastic. An elastomer O-ring 64 and the loop 66 at the pivoting end of the pin are slipped over a cylindrical boss 68 that extends off one of the plastic halves 62 of the tool. When the two plastic halves are brought together in the direction of arrow 70 in FIG. 6, they press the metal loop into the elastomer O-ring, slightly cocking the pin, which also presses the straight section of the pin against one of the plastic halves 62. The pin 40 extends out from the tool body through a slot 72 defined between portions of the two plastics halves 60 and 62. An internal surface 74 on the other plastic half 60 pushes the loop portion of pin 40 into the elastomer O-ring 64 for tension.

Figure 7:
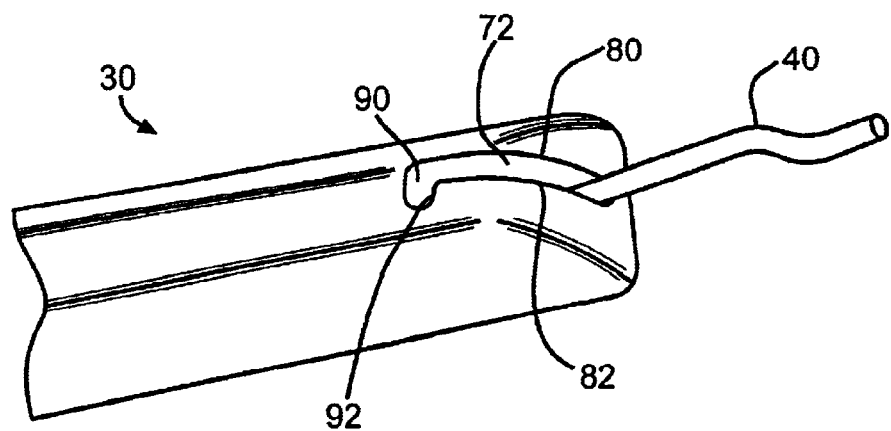
FIG. 7 is a fragmentary perspective view illustrating the key holding means in the tool of the present invention.

FIG. 7 is a fragmentary perspective view illustrating the key holding means in the tool of the present invention. The two halves 60 and 62 of the tool body along with the slot 72 defined therebetween are shown in FIG. 7. Slot 72 extends from the distal end 36 of body in a direction generally parallel to the longitudinal axis 32. As the pin 40 rotates or pivots, it is forced to ride up a slight incline produced by the plastic molded halves of the tool. In particular, the incline is defined by the walls or surfaces 80 and 82 of slot 72 shown in FIG. 7. At the end of rotation, corresponding to a fully activated screw (¼ turn), the pin 40 falls into a small hollow or detent 90 which drops the pin back to its natural plane of rotation. A straight wall 92 prevents the pin from rotating forward. A gently force is needed to raise the pin 40 out of the detent 90 and rotate it back to its forward insertion position after key 40 is disengaged from the expansion screw. Such force can be provided by the finger of the user of tool 30. The forward insertion position corresponds to the beginning of the angular path of key 40 and detent 90 is located at the end of that angular path. The fully activated screw (¼ turn) is the result of pin 40 travelling through an angular path of about 90 degrees.

Figure 8:
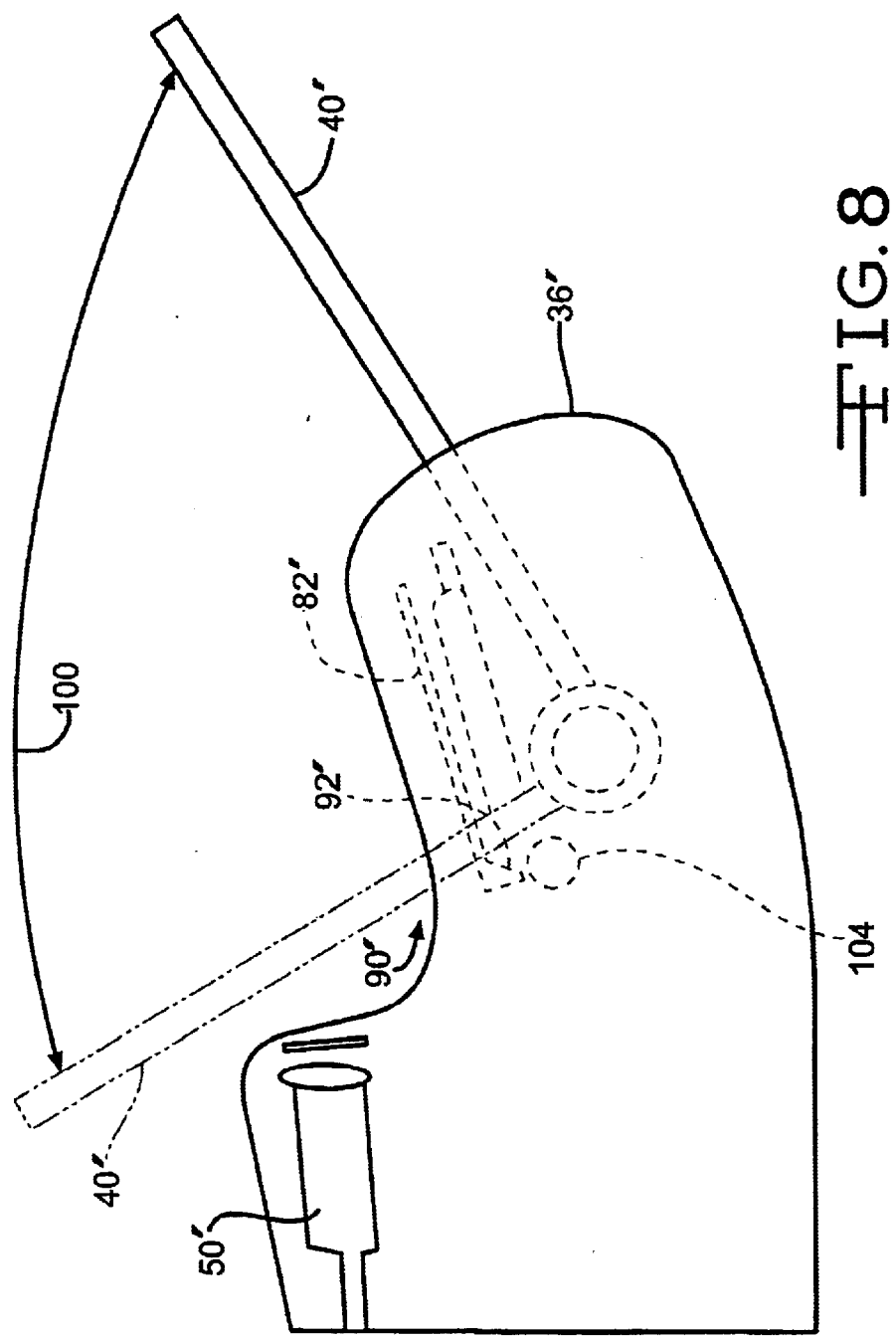
FIG. 8 is a fragmentary sectional view an alternative form of the key holding means and releasing means in the tool of the present invention.

Alternatively, the tool can be provided with manually-operated means carried by the tool body or handle for moving the key out of the detent for return to the beginning of the path after the key is disengaged from the expansion screw. This is illustrated in FIG. 8 which shows a slightly different form of the tool of the present invention. Components of the tool of FIG. 8 which correspond to those of the tool of FIGS. 4–7 are provided with the same reference numeral having a prime designation. The angular path of travel of pin 40' is illustrated by the arrow 100 in FIG. 8 wherein the solid line showing of pin 40' is at the beginning of the angular path and the broken line showing of pin 40' is at the end of the angular path. A manually-operated push button 104 is carried by the body of tool 30' and is located so that upon manual inward pushing of button 104 pin 40' is moved out of the detent. Then the user simply can return pin 40' to the solid line position shown in FIG. 8 by simple finger action.

In another aspect of the present invention, the tool 30 satisfies the need for use of such a tool in the dental/orthodontic operatory. Such a tool must allow sterilization of the front portion that enters the mouth. The contra-angled front portion 42, i.e. its angled disposition relative to the tool longitudinal axis 32, facilitates defining front portion 42 as the only portion which enters the mouth, the handle portion 38 never entering the mouth. Thus front portion 42 can be sterilized and handle portion 38 simply disinfected. Alternatively, a sterilization snap-on front section would attach to a common handle portion. In this way, the battery, switch, and bulb just require a simple disinfection. This also would allow a rechargeable battery to be used. In this case, an LED light source could be used instead of an incandescent lamp.

Alternate methods of capturing, releasing, or restricting rotation of the key or pin can of course be employed. Pin capture with the aid of magnets, spring action, capture of a segment of the wire in a hole, or other known mechanisms can be employed. Rotation of the pin may be limited by the use of the housing design, pins, other known mechanisms.

The method of this invention comprises: 1) visually sighting the insertion hole or bore of an orthodontic expansion screw located in the mouth of a patient, 2) inserting a hand-held tool having a rotatable or pivotal pin at the end thereof into the mouth of the patient, 3) moving the tool so as to rotate or pivot the pin while turning the orthodontic expansion screw, 4) capturing the pin within the tool, 5) disengaging the pin from the orthodontic screw, and 6) removing the tool from the patient's mouth.

The releasable capturing or holding of the key or pin in the tool and method of the present invention upon completion of the turning or activation of the orthodontic expansion screw prevents free and reversible rotation or pivoting of the key or pin. This, in turn, avoids the problem of back driving the expansion screw and negating the activation. The light source carried by the tool facilitates its use by illuminating the screw insertion hole and the end of the pin. The structure of the tool allows for convenient and effective sterilization of the portion of the tool which enters the patient's mouth.

Figure 9:
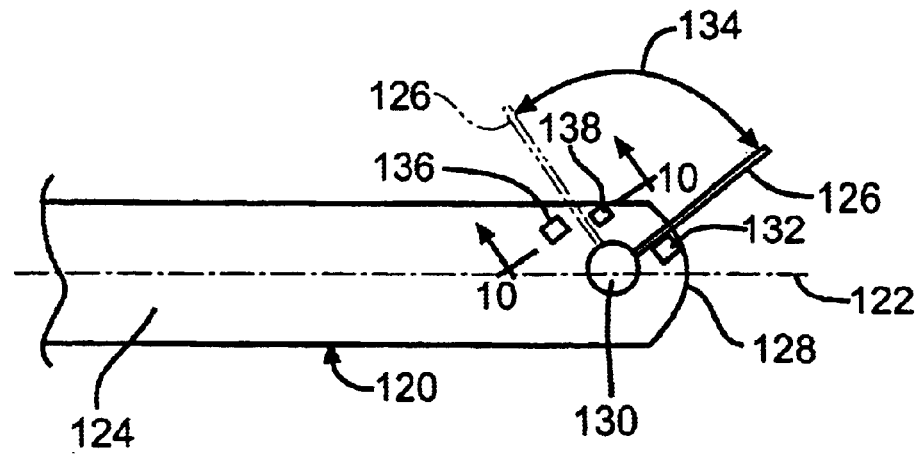
FIG. 9 is a diagrammatic view of an alternative embodiment of the tool according to the present invention.
Figure 10:
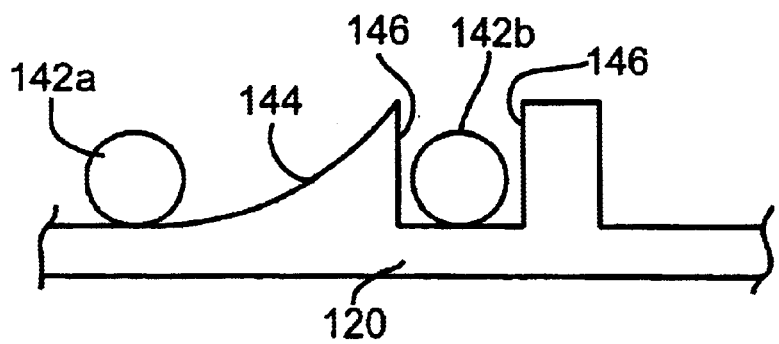
FIG. 10 is a diagrammatic sectional view taken about on line 10—10 in FIG. 9.

FIGS. 9 and 10 illustrate an alternative embodiment of the tool of the present invention. In this embodiment, the key or pin, its pivotal or rotatable connection and the releasable pin holding or capturing means are carried on a handle in the form of an elongated solid strip or bar. Referring to FIG. 9, handle 120 is in the form of a solid elongated strip or bar having a longitudinal axis 122 and a portion 124 for grasping by the hand of a user. The key or pin 126 is located near the distal end 128 of handle 120. The pivotal or rotational connection of pin 126 to handle 120 is designated 130, the axis being substantially perpendicular to longitudinal axis 122. A formation or structure 132 on handle 120 serves as a stop for pin 126 to set the insertion angle. This also defines the beginning of the arcuate path 134 where pin 126 is shown in solid line representation. The pin holding or capturing means is designated 136 and located at the end of the arcuate path 134 where pin 126 is shown in broken line representation. The inclined formation along the path between step 132 and holding means 136 is designated 138. The foregoing is illustrated further in FIG. 10 wherein item 142a illustrates the key or pin riding along the inclined surface 144 provided on handle 120 during movement causing turning or activation of the orthodontic expansion screw, and item 142b illustrates the pin or key having moved or fallen into a well defined by the detent structure 146 on handle 120 which releasably captures the pin.

It is therefore apparent that the present invention accomplishes its intended objectives. While embodiments of the invention have been described in detail, that has been done for the purpose of illustration, not limitation.

What is claimed is:

1. A hand-operated tool for turning orthodontic expansion screws comprising:
   a) an elongated handle having a longitudinal axis and substantially opposite ends and having a portion extending longitudinally from one end for grasping by the hand of a user;
   b) a key in the form of a pin having a shape and size for engaging a structure such as a bore in the orthodontic expansion screw, the key being movably carried by the handle near the other end thereof for unimpeded movement along an angular path in a plane substantially parallel to the longitudinal axis of the handle during engagement between the key and the orthodontic expansion screw structure so that the screw is rotated in response to movement of the handle manually by the user in a direction causing the key to move along the angular path from the beginning of the path to the end of the path, the angular path being defined by a structure extending along the handle; and
   c) holding means on the handle near an end of the structure defining the angular path of the key for releaseably holding the key at the end of the angular path to allow the key to be disengaged from the expansion screw without rotating the screw in an opposite direction.

2. The tool according to claim 1, wherein the key has one end for engaging the structure of the expansion screw and another end pivotably mounted on the handle for movement about an axis substantially perpendicular to the longitudinal axis of the handle.

3. The took according to claim 1, wherein the handle has structures thereon for limiting the angular path of movement of the key to bout ninety degrees.

4. The tool according to claim 1, wherein the holding means comprise:
   a) a slightly inclined formation on the handle along which a portion of the key slides during movement from the beginning of the angular path to the end of the angular path; and
   b) a detent at the end of the inclined formation for capturing the portion of the key when it reaches the end of the angular path.

5. The tool according to claim 4, wherein the detent is shaped and sized to allow the key to be urged manually from the detent for return to the beginning of the path after the key is disengaged from the expansion screw.

6. The tool according to claim 4, further including manually-operated means carried by the handle for moving the key out of the detent for return to the beginning of the path after the key is disengaged from the expansion screw.

7. The tool according to claim 1, further including a light source carried by the handle to assist the user with sighting the key and the structure on the orthodontic expansion screw to be engaged by the key.

8. The tool according to claim 1, wherein the handle is of a length such that when the key engages the orthodontic expansion screw the portion of the handle grasped by the user extends out of the mouth of the patient and only the remainder of the handle on which the key is carried is located in the mouth of the patient so that the remainder can be sterilized separate from the portion of the handle grasped by the user.

9. The tool according to claim 8, wherein the remainder of the handle is detachable to facilitate its sterilization and replacement.

10. The tool according to claim 1, wherein the handle comprises a hollow body having a slot therein near the other end and wherein the key has one end within the hollow body and another end extending through the slot outwardly of the body so that the key moves in the slot along the angular path.

11. The tool according to claim 10, wherein the slot extends in a direction substantially parallel to the longitudinal axis of the handle and serves to limit the angular path of movement of the key to about ninety degrees.

12. A hand-operated tool for turning orthodontic expansion crews comprising:
   a) an elongated tool body having a longitudinal axis an substantially opposite ends, said body having an interior region and an exterior portion extending longitudinally from one end for grasping by the user, said body having a longitudinally extending slot near the other end thereof;
   b) a key in the form of a pin having a shape and size for engaging a structure such as a bore in the orthodontic expansion screw, the key having one end for engaging the structure of the screw and another end pivotally mounted to the body in the interior region thereof near the other end thereof, the key extending through the slot in the body, so that during engagement between the key and the orthodontic expansion screw structure the screw is rotated in response to movement of the tool body manually by the user causing the one end of the key to move along an angular path in a plane substantially parallel to the longitudinal axis of the tool body from the beginning of the path to the end of the path during engagement between the key and the orthodontic expansion screw; and c) holding means carried by the tool body near the other end thereof and near the end of the angular path of the one end of the key for releasably holding the key at the end of the angular path to allow the key to be disengaged from th expansion screw without rotating the screw in an opposite direction.

13. The tool according to claim 12, wherein the one end of the key is pivot ally mounted for movement about an axis substantially perpendicular to the longitudinal axis of the tool body.

14. The tool according to claim 12, wherein the length of the slot and the location where the end of the key is pivotally mounted limit the angular path of movement of the end of the key to about ninety degrees.

15. The tool according to claim 12, wherein the holding means comprises:

a) a slightly inclined formation in the tool body along which a portion of the key slides during movement from the beginning of the angular path to the end of the angular path; and b) a detent at the end of the inclined formation for capturing the portion of the key when it reaches the end of the angular path.

16. The tool according to claim 15, wherein the detent is shaped and sized to allow the key to be urged manually from the detent for return to the beginning of the path after the key is disengaged from the expansion screw.

17. The tool according to claim 15, further including manually-operated means carried by the tool body for moving the key out of the detent for return to the beginning of the path after the key is disengaged from the expansion screw.

18. A method for adjusting orthodontic expansion screws comprising:

a) sighting the insertion hole of an orthodontic expansion screw located in the mouth of a patient;

b) introducing a hand-held tool having a rotatable pin at the end thereof into the mouth of the patient;

c) inserting the pin into the insertion hole;

d) moving the tool so as to pivot the pin along an angular path while turning the orthodontic screw;

e) capturing the pin within the tool when the pin reaches the end of the angular path;

f) disengaging the pin from the orthodontic screw; and g) removing the tool from the patient's mouth.

19. The method according to claim 18, further including illuminating the insertion hole of the expansion screw while introducing the tool and inserting the pin into the hole.

20. A hand-operated tool for turning orthodontic expansion screws comprising:

a) an elongated tool body having a longitudinal axis an substantially opposite ends, said body having interior region and an exterior portion extending longitudinally from one end for grasping by the user, said body having a longitudinally extending sloth near the other end thereof;

b) a key in the form of a pin having a shape and size for engaging a structure such as a bore in the orthodontic expansion screw, the key having one end or engaging the structure of the screw and another end pivotally mounted to the body in the interior region thereof, the key extending through the slot in the body, so that upon engagement between the key and the orthodontic expansion screw structure the screw is rotated in response to movement of the tool body manually by the user causing the one end of the key to move along an angular path in a plane substantially parallel to the longitudinal axis of the tool body from the beginning of the path to the end of the path;

c) holding means carried by the tool body near the end of the angular path of the one end of the key for releasably holding the key at the end of the a regular path to allow the key to be disengaged from the expansion screw without rotating the screw in an opposite direction; and d) a light source carried by the tool body to assist the user with sighting the end of the key and the structure on the orthodontic expansion screw to be engaged by the key.

21. A hand-operated tool for turning orthodontic expansion crews comprising:

a) an elongated tool body having a longitudinal axis and substantially opposite ends, said body having an interior region and an exterior portion extending longitudinally from one end for grasping by the user, said body having a longitudinally extending slot near the other end thereof;

b) a key in the form of a pin having a shape and size for engaging a structure such as a bore in the orthodontic expansion screw, the key having one end for engaging the structure of the screw and another end pivotally mounted to the body in the interior region thereof, the key extending through the slot in the body, so that upon engagement between the key and the orthodontic expansion screw structure the screw is rotated in response to movement of the tool body manually by the user causing the one end of the key to move along an angular path in a plane substantially parallel to the longitudinal axis of the tool body from the beginning of the path to the end of the path;

c) holding means carried by the tool body near the end of the angular path of the one end of the key for releasably holding the key at the end of the angular path to allow the key to be disengaged from the expansion screw without rotating the screw in an opposite direction.

d) the too body being of a length such that when the key engages the orthodontic expansion screw the portion of the tool body grasped by the user extends out of the mouth of the patient and only the remainder of the tool body in which the key is carried is located in the mouth of the patient so that the remainder can be sterilized separate from the portion of the tool body grasped by the user; and e) the remainder of the tool body is detachable to facilitate its sterilization and replacement.

* * * * *

UNITED STATES PATENT AND TRADEMARK OFFICE
CERTIFICATE OF CORRECTION

PATENT NO. : 6,786,718 B2
DATED : September 7, 2004
INVENTOR(S) : Lauren et al.

It is certified that error appears in the above-identified patent and that said Letters Patent is hereby corrected as shown below:

Column 6,
Line 15, "took" should read -- tool --
Line 17, "bout" should read -- about --
Line 60, "crews" should read -- screws --
Line 61, "an" should read -- and --

Column 7,
Line 18, "th" should read -- the --
Line 21, "pivot ally" should read -- pivotally --
Line 64, "an" should read -- and --
Line 65, after "having" insert -- an --

Column 8,
Line 3, "sloth" should read -- slot --
Line 7, "or" should read -- for --
Line 20, "a regular" should read -- angular --
Line 51, change period at end of sentence to a semi-colon.
Line 52, "too" should read -- tool --

Signed and Sealed this

Third Day of May, 2005

JON W. DUDAS
*Director of the United States Patent and Trademark Office*